US011162933B2

(12) United States Patent
Chatterjee et al.

(10) Patent No.: US 11,162,933 B2
(45) Date of Patent: Nov. 2, 2021

(54) SYSTEM AND METHOD FOR DETECTING HEAVY METALS IN A FLUID

(71) Applicant: Haier US Appliance Solutions, Inc., Wilmington, DE (US)

(72) Inventors: Somak Chatterjee, Hyderabad (IN); Gregory Sergeevich Chernov, Louisville, KY (US); Andrew Reinhard Krause, Louisville, KY (US); Sharath Chandra Prasad, Hyderabad (IN); Praveena Alangar Subrahmanya, Vittal (IN)

(73) Assignee: Haier US Appliance Solutions, Inc., Wilmington, DE (US)

( * ) Notice: Subject to any disclaimer, the term of this patent is extended or adjusted under 35 U.S.C. 154(b) by 0 days.

(21) Appl. No.: 16/567,137

(22) Filed: Sep. 11, 2019

(65) Prior Publication Data

US 2021/0072214 A1    Mar. 11, 2021

(51) Int. Cl.
*G01N 33/18* (2006.01)
*C02F 1/00* (2006.01)
*C02F 101/22* (2006.01)
*B01D 37/04* (2006.01)

(52) U.S. Cl.
CPC ......... *G01N 33/1813* (2013.01); *C02F 1/004* (2013.01); *G01N 33/1893* (2013.01); *B01D 37/043* (2013.01); *C02F 2101/22* (2013.01)

(58) Field of Classification Search
CPC ............ G91N 22/1813; G91N 22/1893; C02F 2101/20; G01N 33/1813; G01N 33/1893
See application file for complete search history.

(56) References Cited

U.S. PATENT DOCUMENTS

| 3,403,081 | A | * | 9/1968 | Rohrback | C12Q 1/001 205/777.5 |
| 3,838,774 | A | * | 10/1974 | Dolan | B01J 47/14 210/85 |
| 3,990,066 | A | * | 11/1976 | Malmgren | B01D 61/12 340/603 |
| 4,806,912 | A | * | 2/1989 | Clack | B01D 61/12 210/85 |
| 4,937,557 | A | * | 6/1990 | Tucci | B01D 61/12 210/85 |
| 5,087,883 | A | * | 2/1992 | Hoffman | G01N 27/07 210/96.1 |

(Continued)

FOREIGN PATENT DOCUMENTS

| CN | 102135518 B | 5/2013 |
| CN | 203101324 U | 7/2013 |
| CN | 105842323 B | 6/2018 |

*Primary Examiner* — John Fitzgerald
(74) *Attorney, Agent, or Firm* — Dority & Manning, P.A.

(57) ABSTRACT

A system and method are directed to detecting the presence of heavy metals in a flowing fluid, such as a drinking water supply. The system includes a first chamber for receiving a filtered portion of the fluid and a second chamber for receiving an unfiltered portion of the fluid. A test device measures electrical properties of the filtered fluid in the first chamber and the unfiltered fluid in the second chamber, such as an electric potential difference, and a controller can use the measured electrical properties to detect the presence or quantity of one or more heavy metals within the fluid, such as lead, cadmium, zinc, nickel, and/or copper.

17 Claims, 4 Drawing Sheets

(56) References Cited

U.S. PATENT DOCUMENTS

| | | | | |
|---|---|---|---|---|
| 5,200,106 | A * | 4/1993 | Hoots | G01N 33/1813 210/697 |
| 5,450,358 | A * | 9/1995 | Seibert | B01D 61/12 210/94 |
| 5,580,444 | A * | 12/1996 | Burrows | B01D 61/08 210/110 |
| 6,453,257 | B1 * | 9/2002 | Juhasz | B01D 46/44 702/114 |
| 6,619,112 | B2 * | 9/2003 | Juhasz | B01D 46/44 73/168 |
| 6,699,384 | B1 | 3/2004 | Lin et al. | |
| 7,208,123 | B2 * | 4/2007 | Knollenberg | G01N 29/022 422/400 |
| 7,883,617 | B2 * | 2/2011 | Einaga | G01N 33/1813 205/789.5 |
| 7,897,032 | B2 | 3/2011 | Viltchinskaia et al. | |
| 9,589,686 | B2 * | 3/2017 | Potyrailo | G21C 17/022 |
| 9,970,899 | B2 * | 5/2018 | Sankaran | G01N 27/333 |
| 10,175,221 | B2 * | 1/2019 | Ciampini | G01N 33/2882 |
| 2001/0039465 | A1 * | 11/2001 | Schultz | G05B 15/02 700/282 |
| 2003/0078751 | A1 * | 4/2003 | Juhasz | G01N 15/0826 702/114 |
| 2003/0235926 | A1 * | 12/2003 | Knollenberg | G01N 29/222 436/181 |
| 2008/0116908 | A1 * | 5/2008 | Potyrailo | G01N 33/1893 324/721 |
| 2010/0028648 | A1 * | 2/2010 | de Zwart | B29C 45/0053 428/304.4 |
| 2010/0237018 | A1 * | 9/2010 | Hollebone | G01N 33/1826 210/662 |
| 2011/0186449 | A1 * | 8/2011 | Clochard | G01N 27/31 205/793 |
| 2011/0284395 | A1 * | 11/2011 | Dimitrakopoulos | G01N 27/42 205/789 |
| 2012/0114089 | A1 * | 5/2012 | Potyrailo | G01N 27/126 376/247 |
| 2012/0205533 | A1 * | 8/2012 | Ariya | G01N 1/405 250/282 |
| 2015/0104792 | A1 * | 4/2015 | Mazumdar | G01N 21/6428 435/6.11 |
| 2015/0253265 | A1 * | 9/2015 | Whitten | G01N 25/4826 506/9 |
| 2015/0369775 | A1 * | 12/2015 | Caroli Rezende | G01N 27/49 205/782 |
| 2017/0003261 | A1 * | 1/2017 | Li | C09B 67/0083 |
| 2017/0219556 | A1 * | 8/2017 | Ciampini | G01N 27/126 |
| 2018/0017526 | A1 * | 1/2018 | Sankaran | G01N 27/48 |
| 2018/0118351 | A1 * | 5/2018 | Fox | B64D 13/00 |
| 2018/0246059 | A1 * | 8/2018 | Kurup | G01N 33/1813 |
| 2018/0251947 | A1 * | 9/2018 | Stone | B01F 15/00175 |
| 2019/0175104 | A1 * | 6/2019 | Malik | A61B 5/0002 |
| 2019/0219539 | A1 * | 7/2019 | Huang | B01D 53/80 |
| 2019/0302087 | A1 * | 10/2019 | Kahn | G01N 33/1813 |
| 2019/0339246 | A1 * | 11/2019 | Johnson, Jr. | G01N 27/4145 |
| 2020/0033314 | A1 * | 1/2020 | Schwabacher | C09B 29/3673 |
| 2020/0047093 | A1 * | 2/2020 | Bono | G01N 1/10 |
| 2020/0225204 | A1 * | 7/2020 | Chatterjee | G01N 33/18 |

* cited by examiner

SYSTEM AND METHOD FOR DETECTING HEAVY METALS IN A FLUID

FIELD OF THE INVENTION

The present subject matter relates generally to the detection of heavy metals within a fluid, and more particularly to assemblies for detecting heavy metals or other specific contaminants in a water supply.

BACKGROUND OF THE INVENTION

Water supply systems are often intended to distribute water from a central source, such as a water tower or river, to consumers for use or consumption. It is important that such water supply systems contain suitable water filtering and treatment plants for removing harmful contaminants from the water prior to human consumption. As water passes through the pipes that make up the water supply system, the water quality can degrade by chemical reactions, biological processes, and pipe corrosion, leaching, or degradation. For example, pipes under water in old buildings can leach lead and other heavy metals or contaminants like cadmium, zinc, nickel, and copper into the water, which may be particularly harmful for human health.

Although there are processes for testing for lead or other heavy metals in drinking water, such tests are typically complicated, costly, and require samples to be mailed off to a lab for testing. Thus, existing methods of detecting harmful metals in drinking water are rarely used due to the high cost and delay time involved in sample measurement from certified laboratory or electrode assembly. Furthermore, in the absence of instantaneous lead measurement devices, customers may remain unaware of harmful heavy metals they are consuming, and thus not perform suitable point-of-use filtration before consumption.

Accordingly, improved systems and methods for detecting contaminants within a drinking water supply system would be useful. More specifically, a contaminant detection assembly that may be mounted inline for providing instantaneous feedback regarding the presence of harmful heavy metals within a water supply would be particularly beneficial.

BRIEF DESCRIPTION OF THE INVENTION

Aspects and advantages of the invention will be set forth in part in the following description, or may be apparent from the description, or may be learned through practice of the invention.

In one exemplary embodiment, a system for detecting a contaminant in a fluid is provided. The system includes a first chamber for receiving a filtered portion of the fluid and a second chamber for receiving an unfiltered portion of the fluid. A test device is provided for measuring electrical properties of the filtered portion of the fluid in the first chamber and the unfiltered portion of the fluid in the second chamber and a controller is operably coupled to the test device, the controller being configured for detecting the contaminant within the fluid based at least in part on the measured electric properties.

In another exemplary embodiment, a method for detecting a contaminant in a fluid is provided. The method includes providing a filtered portion of the fluid to a first chamber, providing an unfiltered portion of the fluid to a second chamber, measuring electrical properties of the filtered portion of the fluid in the first chamber and the unfiltered portion of the fluid in the second chamber using a test device, and detecting the presence or quantity of the contaminant based at least in part on the measured electric properties.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

Repeat use of reference characters in the present specification and drawings is intended to represent the same or analogous features or elements of the present invention.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Figure 1:
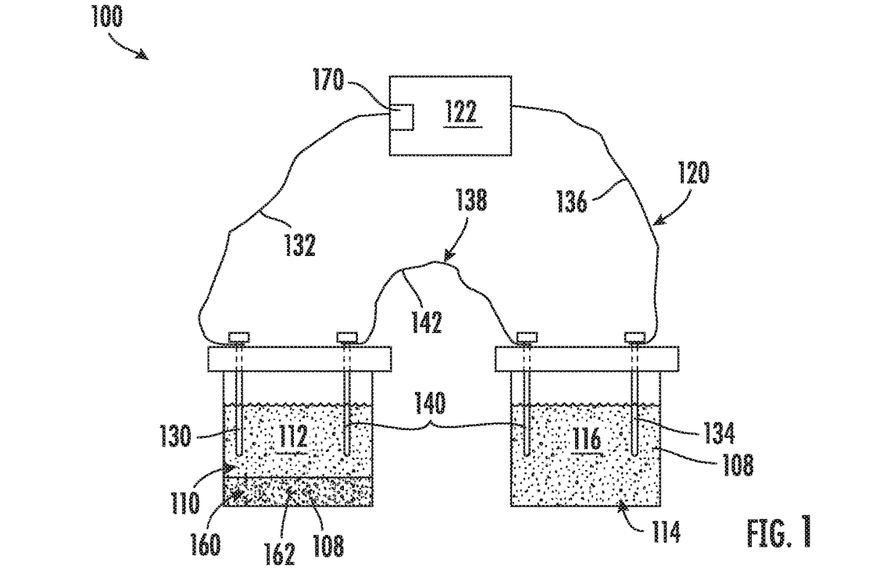
FIG. 1 provides a perspective view of a laboratory setup of a static contaminant detection assembly for detecting specific contaminants according to an exemplary embodiment of the present subject matter.
Figure 2:
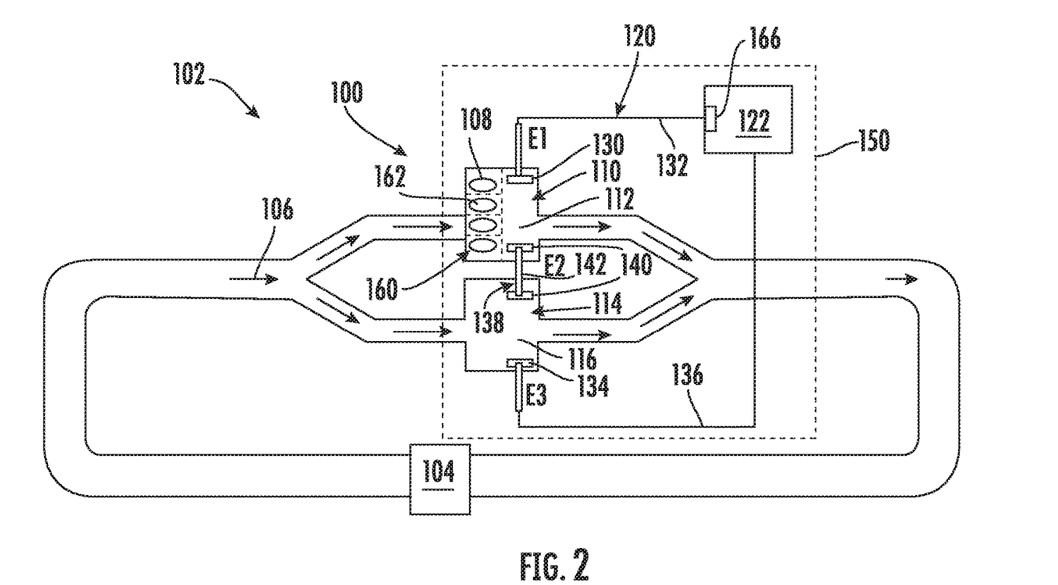
FIG. 2 is a schematic diagram of a dynamic contaminant detection assembly according to an exemplary embodiment of the present subject matter.

Referring now to FIGS. 1 and 2, a contaminant detection system, referred to herein simply as detection system 100, will be described according to an exemplary embodiment of the present subject matter. Specifically, FIG. 1 illustrates a simplified schematic laboratory setup to facilitate discussion of the operation of the detection system 100. FIG. 2 illustrates an exemplary water supply system 102 within which detection system 100 may be used.

As explained below, detection system 100 may generally be used for detecting the presence, quantity, or concentration of contaminants within a flow of fluid or a fluid sample, illustrated herein as a flow of water 106 from water supply system 102. Water supply system 102 may generally include a water supply source 104, which may include a system of filtration tanks and subsystems, such that the flow of water 106 is intended to be clean and substantially free of contaminants and harmful chemicals. However, as explained briefly above, under certain conditions and circumstances, such water 106 may nonetheless have harmful contaminants, heavy metals, or other chemicals which are undesirable. As shown, detection system 100 operates instantaneously and inline with water supply system 102 for direct and accurate contaminant detection.

As described herein, detection system 100 is configured for detecting the presence of specific contaminants, such as heavy metals (identified in FIGS. 1 and 2 by reference numeral 108), such as lead, cadmium, copper, and chromium, which may be present in drinking water supply systems and may present health problems when used for human consumption. However, it should be appreciated that aspects of detection system 100 may be used in alternative embodiments to detect the presence of any contaminant in any fluid, and that the terms specific contaminant, contaminant, heavy metals, and the like, may be used interchangeably herein. The specific application described herein is intended only to explain aspects of the present subject matter and is not intended to be limiting in any manner.

As illustrated in the figures, detection system 100 includes a first chamber 110 which is configured for receiving a filtered portion of the fluid, identified herein as filtered fluid 112. In addition, detection system 100 includes a second chamber 114 which is configured for receiving an unfiltered portion of the fluid, identified herein as unfiltered fluid 116. As used herein, the term "filtered fluid" and the like are intended to refer to a portion of water 106 which has been treated, screened, or otherwise filtered to remove at least one contaminant, such as heavy metals 108. By contrast, the term "unfiltered fluid" and the like are intended to refer to a flow of water 106 that has not been treated and which may be used for comparison with filtered fluid 112, as described in more detail below.

Notably, filtered fluid 112 and unfiltered fluid 116 may have different electrical properties which may be measured and used to determine the presence, quantity, or concentration of a particular heavy metal 108 within water 106. For example, the electric potential, voltage, conductivity, ionization potential, or other measurable electrical property of filtered fluid 112 and unfiltered fluid 116 may vary and may be detected by a microcontroller or detection system. Specifically, as illustrated, detection system 100 may include a test device 120 for measuring the electrical properties of filtered fluid 112 and unfiltered fluid 116. Test device 120 may be operably coupled with a controller 122 which may monitor the electrical properties and may be programmed for determining the presence, quantity, or concentration of one or more heavy metals 108 within water 106.

As used herein, "processing device" or "controller" may refer to one or more microprocessors and is not restricted necessarily to a single element. The processing device or controller 122 can be programmed to operate detection system 100, test device 120, and other components. The processing device may include, or be associated with, one or more memory elements (e.g., non-transitory storage media). In some such embodiments, the memory elements include electrically erasable, programmable read only memory (EEPROM). Generally, the memory elements can store information accessible processing device, including instructions that can be executed by processing device. Optionally, the instructions can be software or any set of instructions and/or data that when executed by the processing device, cause the processing device to perform operations.

In addition, test device 120 may be any suitable measurement device or system of devices which can be used to measure electrical properties of first chamber 110 and second chamber 112 which may be suitable for use in estimating or determining the presence of a contaminant, such as a heavy metal 108, within a fluid such as water 106. According to the illustrated embodiment, test device 120 is a potential measurement device configured for measuring an electric potential of filtered fluid 112, unfiltered fluid 116, or an electric potential difference between filtered fluid 112 and unfiltered fluid 116. Alternatively, test device 120 may measure a voltage, conductivity, ionization potential, or other suitable properties within first chamber 110 and second chamber 112. Although an exemplary setup and method of operating test device 120 will be described below, it should be appreciated that variations and modifications may be made to detection system 100 and test device 120 while remaining within scope of the present subject matter.

As shown, potential measurement device or test device 120 includes a first electrode 130 positioned within first chamber 110 such that it contacts filtered fluid 112. First electrode 130 may be electrically coupled with controller 122 via a first electrical wire 132. Similarly, a second electrode 134 may be positioned within second chamber 114 such that it contacts unfiltered fluid 116. Second electrode 134 may be electrically coupled with controller 122 via a second electrical wire 136. In addition, a bridge assembly 138 may be electrically coupled with both filtered fluid 112 and unfiltered fluid 116. More specifically, a bridge electrode 140 may be positioned in each of first chamber 110 and second chamber 114 to contact filtered fluid 112 and unfiltered fluid 116, respectively. A bridge wire 142 may extend between and electrically couple bridge electrodes 140.

In this manner, a closed electrical circuit including controller 122, first chamber 110, and second chamber 114 is created which controller 122 may use to detect changes in electric potential or other electrical properties. Each of electrodes 130, 134 and 140 may be formed from any material suitable for facilitating the measurement of electrical properties of filtered fluid 112 and unfiltered fluid 116. According to an exemplary embodiment, these electrodes 130, 134, and 140 are made of noble metals, such as gold, silver, platinum, and/or titanium. Alternatively, these electrodes 130, 134, and 140 may be made from stainless steel, graphite, graphene, and/or graphene oxide.

Although a basic laboratory set up is illustrated in FIG. 1, it should be appreciated that detection system 100 can be embodied in a much more compact form. For example, according to an exemplary embodiment illustrated schematically in FIG. 2, detection system may be positioned on a printed circuit board or may be embodied as a single micro-electromechanical system (MEMS) 150. In this regard, first chamber 110 and second chamber 114 may be very small (e.g. microscopic) reservoirs for containing a small amount of filtered fluid 112 and unfiltered fluid 116, respectively. In addition, electrodes 130, 134, and 140 as well as wires 132, 136, and 142 may be electrical contacts formed similar to a printed circuit board or formed by micro-fabrication.

According to exemplary embodiments, a filtering system or device is desirable in order to supply first chamber 110 and second chamber 114 with filtered fluid 112 and unfiltered fluid 116 from a single water supply, e.g., water 106. According to the illustrated embodiment, first chamber 110 contains a filter media 160 which is configured for filtering heavy metals 108 from water 106 to create filtered fluid 112. Specifically, filter media 160 may include filter beads 162 that are configured for absorbing a specific heavy metal 108. Although the term "filter" is used herein to describe the removal or collection of contaminants, it should be appreciated that this term is used generally to refer to any chemical removal, such as adsorption or coordinate bond/chelation of a contaminant from a fluid. For example, filter beads 162 may be designed to uptake lead from water 106. Thus, test device 120 may measure filtered fluid 112 with the absence of such lead and a comparison may be made with the same water 106 in its unfiltered form, e.g., unfiltered fluid 116.

During operation, detection system 100 may operate by receiving periodic samples of water 106 or by receiving a continuous stream of water 106. Controller 122 may continuously monitor test device 120 to detect changes in electrical properties of first chamber 110 and second chamber 114. In addition, controller 122 may include a database or data tables which correlate such electrical properties with the presence, quantity, or concentration of particular heavy metals 108. Moreover, controller 122 may be configured for providing a notification when the measured electrical properties indicate that a concentration of heavy metals 108 within water 106 exceeds a predetermined threshold.

As described herein, detection system 100 includes two chambers and may generally be used for detecting the presence of a single heavy metal 108. However, it should be appreciated that according to alternative embodiments, detection system 100 may include additional chambers which may include additional and/or different filter media 160 for facilitating the detection or quantitative measurement of a different heavy metal 108. In this regard, first chamber 110 may include filter beads 162 for absorbing lead, second chamber 114 may receive unfiltered water 106, a third chamber (not shown) may include filter beads 162 for absorbing copper from water 106, and a fourth chamber (not shown) may include filter beads 162 for absorbing chromium from water 106. Test device 120 may be operably coupled with these additional chambers and controller 122 may be configured for comparing electrical properties between each of first chamber 110, third chamber, and fourth chamber with electrical properties of unfiltered fluid 116 in second chamber 114. In this manner, controller 122 may determine the presence of, quantity of, or concentration of any suitable number of contaminants, such as heavy metals 108.

Although test device 120 is described herein as being a system of electrodes positioned within first chamber 110 and second chamber 114, it should be appreciated that other devices and electrical circuits/setups may be used to determine the electrical properties while remaining within scope of the present subject matter. For example according to another embodiment, an electrostatic rheometer (not shown) may be used to measure ionization energy within a plurality of chambers and controller 122 may use that ionization energy to detect the quantity of a particular heavy metal 108. However, it should be appreciated that other suitable devices may be used to measure ionization energy while remaining within the scope of the present subject matter.

In addition, it should be appreciated that detection system 100 may include various additional features or electronic components for improving the detection process and the accuracy of heavy metal detection. For example, controller 122 may include a capacitive filter 166 for reducing noise in a signal received by test device 120. In addition, controller 122 may include a system of power supplies, amplifiers, and other devices for boosting or amplifying these tests signals, for reducing polarization and noise, for otherwise improving the accuracy of heavy metal detection.

Figure 3:
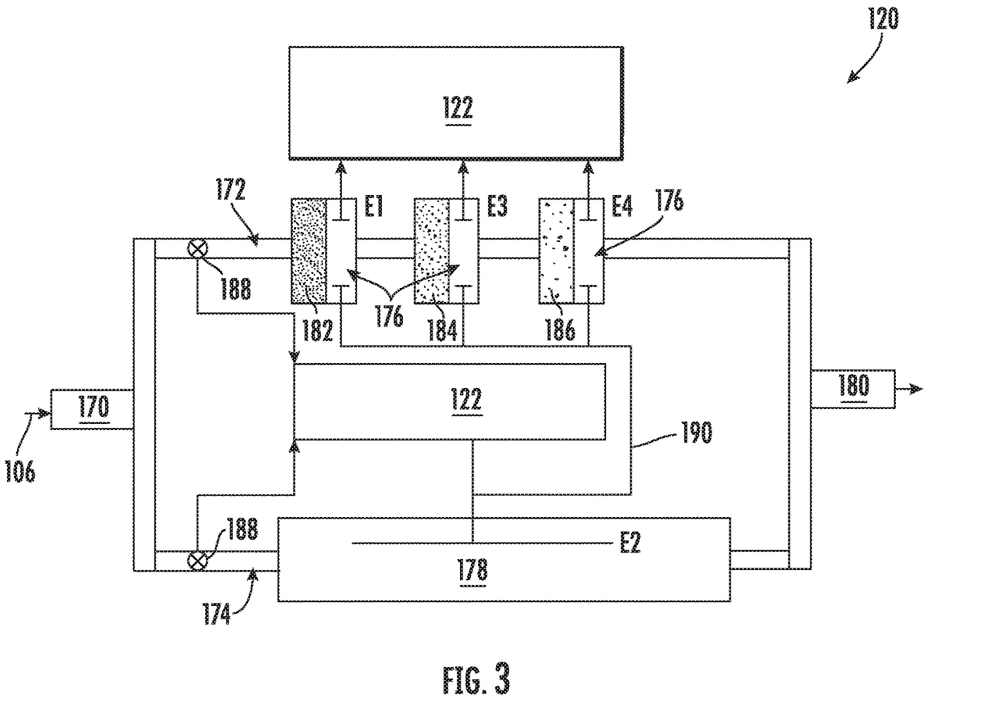
FIG. 3 is a schematic diagram of a dynamic contaminant detection assembly according to another exemplary embodiment of the present subject matter.
Figure 4:
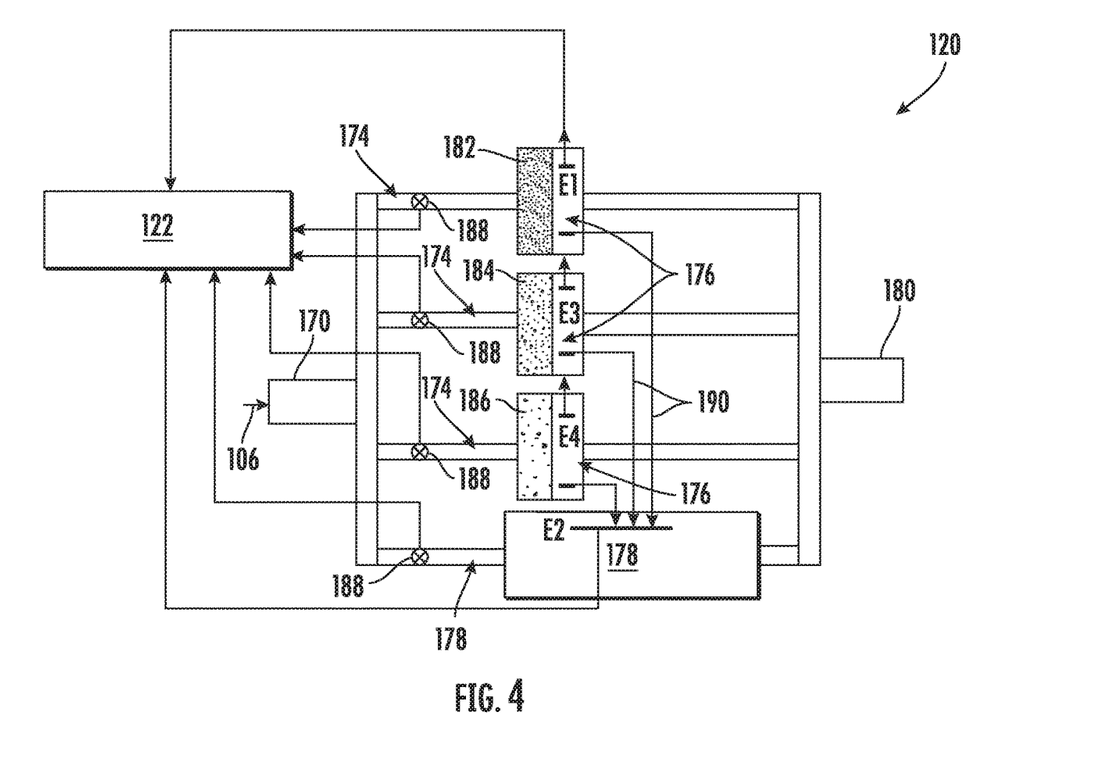
FIG. 4 is a schematic diagram of a dynamic contaminant detection assembly according to yet another exemplary embodiment of the present subject matter.

Referring now briefly to FIGS. 3 and 4, exemplary configurations of detection system 100 will be described according to exemplary embodiments of the present subject matter. Specifically, FIG. 3 illustrates detection system 100 with three test chambers in series and FIG. 4 illustrates detection system 100 with three test chambers in parallel. Due to the similarity with the embodiments described above, like reference numerals will be used to refer to the same or similar features. In addition, also the series embodiment of FIG. 3 is described below, it should be appreciated that the embodiment illustrated in FIG. 4 may operate in a similar manner, but with the filter chambers being fluidly coupled in parallel.

In the embodiment shown in FIG. 3, untreated water 106 passes into test device 120 through an inlet 170. The water 106 then passes through a filtered pathway 172 and an unfiltered pathway 174. The filtered pathway 172 passes through three filter chambers 176 in series, while the unfiltered pathway 174 passes through an unfiltered chamber 178. The filtered pathway 172 and unfiltered pathway 174 may merge downstream of filter chambers 176 and unfiltered chamber 178 before exiting test device 120 through an outlet 180.

Similar to the embodiments described above, each of the filter chambers may include filter media 160 for filtering a particular heavy metal 108 from water 106. Specifically, according to the illustrated embodiment, the first filter chamber 176 contains a lead filter media 182, the second filter chamber 176 contains a copper filter media 184, and the third filter chamber 176 contains a chromium filter media 186. It should be appreciated that test device 120 may alternatively include any suitable number of filter chambers 176, each containing any suitable filter media.

In addition, test device 120 may include one or more valves 188 operably coupled to controller 122 for closing off the inlet, filtered pathway 172, and/or unfiltered pathway 174 when testing is not desired. Test device 120 further includes a system of electrical connections, identified in FIGS. 3 and 4 by reference numeral 190 for clarity. Similar to electrodes 130, 134, wires 132, 136, and bridge assembly 138 described above, electrical connections 190 may be used to facilitate the detection of electric potential or conductivity differences between fluid in filtered pathway 172 and unfiltered pathway 174. Specifically, as illustrated in both FIGS. 3 and 4, electrical connections 190 extend between E2, which is a common bridge, and E1, E3 and E4, which are each sensed independently and compared to E2 to detect electrical conductivity or potential differences to facilitate contaminant detection. Moreover, because various filter media 182-186 is used, electrical potential may be determined between each of filter chambers 176 and unfiltered chamber 178 to determine the amount or concentration of each specific contaminant, e.g., lead, copper, and chromium according to the exemplary embodiment.

Now that the construction of detection system 100 and the configuration of controller 122 according to exemplary embodiments have been presented, an exemplary method 200 of operating a detection system for detecting the presence, quantity, or concentration of contaminants within a fluid will be described. Although the discussion below refers to the exemplary method 200 of operating detection system 100, one skilled in the art will appreciate that the exemplary method 200 is applicable to the operation of a variety of other system configurations and methods of operation. In exemplary embodiments, the various method steps as disclosed herein may be performed by controller 122.

Figure 5:
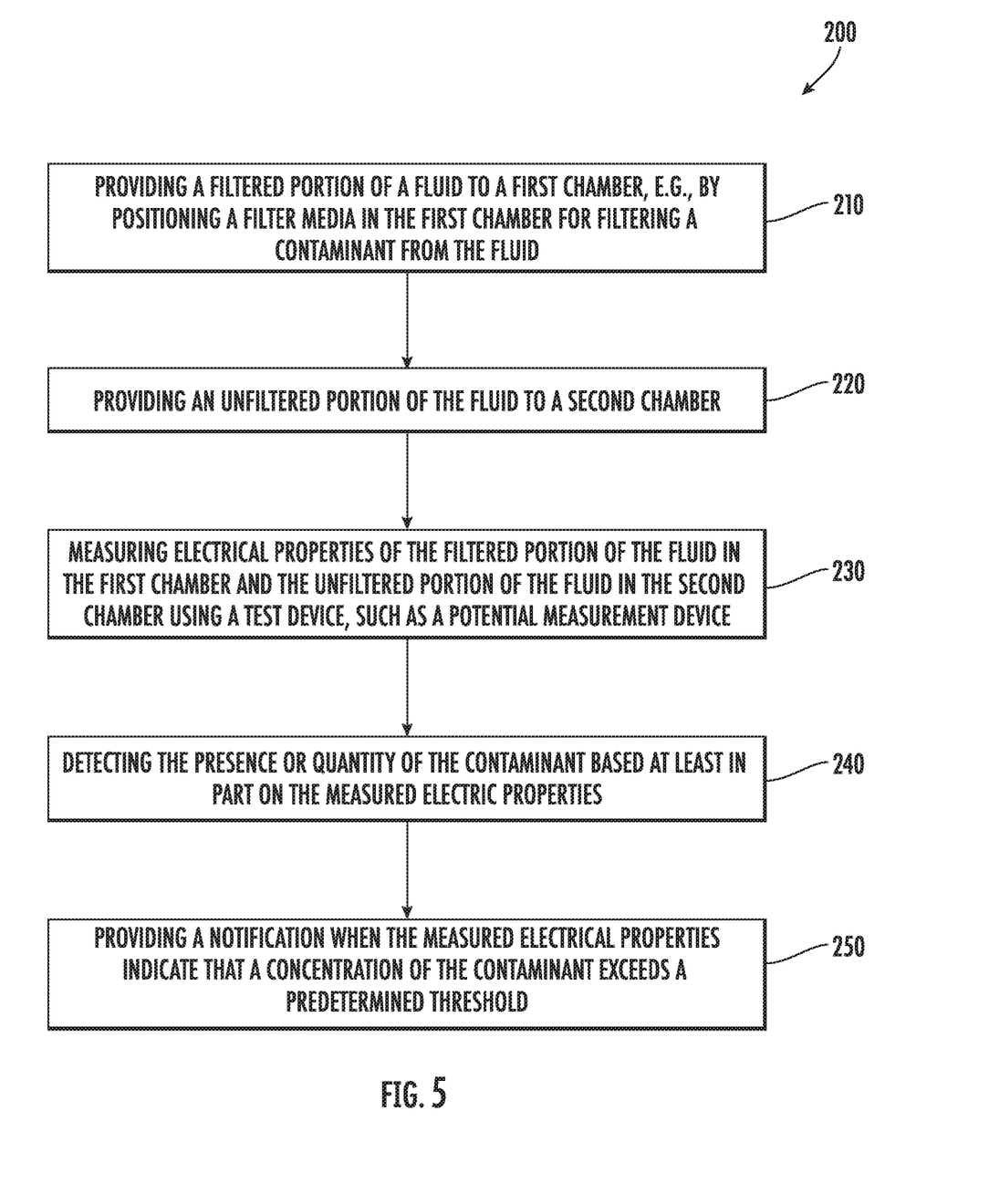
FIG. 5 illustrates a method for detecting specific contaminants in a water supply according to an exemplary embodiment of the present subject matter.

Referring now to FIG. 5, method 200 includes, at step 210, providing a filtered portion of a fluid to a first chamber. For example, a flow of water 106 may be provided into first chamber 110, where the filter beads 162 or another suitable filter media 160 is configured for filtering a particular heavy metal 108 from that fluid to create filtered fluid 112. Step 220 includes providing an unfiltered portion of the fluid to a second chamber. For example, water 106 may be provided into second chamber 114 as unfiltered fluid 116, e.g., untreated or not screened for heavy metals 108.

Step 230 includes measuring electrical properties of the filtered portion of fluid in the first chamber and the unfiltered portion of the fluid in the second chamber using a test device. For example, the test device may be a potential measurement device which includes electrodes 130, 134, and 140 positioned within first chamber 110 and second chamber 114 and being electrically coupled to controller 122 to facilitate the detection of electric potential differences between filtered fluid 112 and unfiltered fluid 116.

Step 240 includes detecting the presence or quantity of the heavy metal based at least in part on the measured electrical properties. In this regard, controller 122 may include a database or lookup table which the associates the measured electrical properties with a specific quantity or concentration of heavy metals 108. Step 250 may include providing a notification when the measured electrical properties indicate that a concentration of the heavy metal exceeds a predetermined threshold. In this regard, controller 122 may be preprogrammed with a safety threshold for one or more heavy metals 108. Controller 122 may monitor the quantity or the concentration of such heavy metals 108 and may provide a notification to a user or consumer when the concentration exceeds that safety threshold.

FIG. 5 depicts steps performed in a particular order for purposes of illustration and discussion. Those of ordinary skill in the art, using the disclosures provided herein, will understand that the steps of any of the methods discussed herein can be adapted, rearranged, expanded, omitted, or modified in various ways without deviating from the scope of the present disclosure. Moreover, although aspects of method 200 are explained using detection system 100 as an example, it should be appreciated that these methods may be applied to the operation of any suitable detection system for detecting contaminants such as heavy metals within a fluid.

The system and method described herein provides for the measurement and/or detection of heavy metals within a water supply using a plurality of electrodes and a dual chamber. A first chamber contains a filtering device which filters heavy metals from water in the first chamber. By contrast, a second chamber receives water from the same supply, but contains no filtering device. Both chambers have two electrodes immersed inside the solution, with one electrode being connected between the two chambers. By monitoring the voltage/conductivity difference between the filtered water in the first chamber and the unfiltered water in the second chamber, a quantitative assessment of heavy metals can be obtained by calibrating voltage difference with concentration. This voltage difference can be magnified further by using an amplifier in series and the concentration polarization can be minimized to get a stable signal by using an AC signal generator. The electrodes could be made of noble metals, like, gold, silver, platinum, and/or titanium. The specific type of heavy metals detected can be controlled by programming the conductivity of heavy metals in the microcontroller.

There are many advantages of such a system and method for measuring or detecting heavy metals in a water supply. For example, the system may be installed inline at a point-of-use location in a commercial or residential setting for instantaneous feedback regarding water quality. In addition, the system may be used continuously or may be reusable simply by replacing the filtering media or device when its capacity is reached. Moreover, the system may help in detecting the life of the filter and its efficiency in removal of such heavy metals. Moreover, such a system will be compact, highly cost effective in comparison to lab testing, and highly effective at detecting contaminants within a water supply.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A system for detecting a contaminant in a fluid, the system comprising:
   a first chamber for receiving a filtered portion of the fluid;
   a second chamber for receiving an unfiltered portion of the fluid;
   a test device for measuring electrical properties of the filtered portion of the fluid in the first chamber and the unfiltered portion of the fluid in the second chamber, wherein the test device is a potential measurement device for measuring an electric potential of the filtered portion of the fluid, an electric potential of the unfiltered portion of the fluid, or an electric potential difference between the filtered portion of the fluid and the unfiltered portion of the fluid; and
   a controller operably coupled to the test device, the controller being configured for detecting the contaminant within the fluid based at least in part on the measured electric properties, wherein the potential measurement device comprises a first electrode positioned within the first chamber, a second electrode positioned within the second chamber, and a bridge electrode positioned within both the first chamber and the second chamber, the bridge electrode bypassing the controller to directly electrically couple the filtered portion of the fluid and the unfiltered portion of the fluid.

2. The system of claim 1, wherein each of the first electrode, the second electrode, and the bridge electrode comprise at least one of gold, silver, platinum, titanium, stainless steel, graphite, graphene, or graphene oxide.

3. The system of claim 1, wherein the test device is a conductivity measurement device for measuring an electric conductivity of the filtered portion of the fluid, an electric conductivity of the unfiltered portion of the fluid, or an electric conductivity difference between the filtered portion of the fluid and the unfiltered portion of the fluid.

4. The system of claim 1, wherein the controller is configured for providing a notification when the measured electrical properties indicate that a concentration of the contaminant exceeds a predetermined threshold.

5. The system of claim 1, wherein the contaminant comprises at least one of lead, cadmium, copper, and chromium.

6. The system of claim 1, wherein the fluid is water from a water supply system.

7. The system of claim 1, wherein the first chamber, the second chamber, the test device, and the controller are mounted on a single printed circuit board.

8. The system of claim 1, wherein the system is embodied as a single microelectromechanical system (MEMS).

9. The system of claim 1, further comprising:
a third chamber for receiving a secondary filtered portion of the fluid, and wherein the test device is electrically connected to the third chamber.

10. The system of claim 1, wherein the test device is an electrostatic rheometer.

11. The system of claim 1, further comprising:
a capacitive filter for reducing noise in a signal received by the test device.

12. The system of claim 1, wherein the first chamber contains a filter media for filtering the contaminant from the fluid to create the filtered portion of the fluid.

13. The system of claim 12, wherein the filter media comprises filter beads configured for absorbing the contaminant.

14. A method for detecting a contaminant in a fluid, the method comprising:
providing a filtered portion of the fluid to a first chamber;
providing an unfiltered portion of the fluid to a second chamber;
measuring electrical properties of the filtered portion of the fluid in the first chamber and the unfiltered portion of the fluid in the second chamber using a test device, wherein measuring the electrical properties comprises positioning a first electrode within the first chamber, positioning a second electrode within the second chamber, positioning a bridge electrode within both the first chamber and the second chamber, wherein the bridge electrode bypass the controller to directly electrically couple the filtered portion of the fluid and the unfiltered portion of the fluid; and
detecting the presence or quantity of the contaminant based at least in part on the measured electric properties.

15. The method of claim 14, wherein measuring the electrical properties comprises:
measuring, using a potential measurement device, an electric potential of the filtered portion of the fluid, an electric potential of the unfiltered portion of the fluid, or an electric potential difference between the filtered portion of the fluid and the unfiltered portion of the fluid.

16. The method of claim 14, further comprising:
creating the filtered portion of the fluid by positioning a filter media in the first chamber for filtering the contaminant from the fluid.

17. The method of claim 14, further comprising:
providing a secondary filtered portion of the fluid to a third chamber; and
measuring electrical properties of the third chamber using the test device, wherein the test device is an electrostatic rheometer for measuring an ionization energy or potential.

* * * * *